US008322348B2

(12) United States Patent
Mirkov et al.

(10) Patent No.: US 8,322,348 B2
(45) Date of Patent: *Dec. 4, 2012

(54) METHODS AND SYSTEMS FOR LASER TREATMENT USING NON-UNIFORM OUTPUT BEAM

(75) Inventors: Mirko Georgiev Mirkov, Chelmsford, MA (US); Rafael Armando Sierra, Palmer, MA (US); George E. S. Cho, Hopkinton, MA (US)

(73) Assignee: Cynosure, Inc., Westford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/947,310

(22) Filed: Nov. 16, 2010

(65) Prior Publication Data

US 2011/0152847 A1  Jun. 23, 2011

Related U.S. Application Data

(63) Continuation of application No. 11/347,672, filed on Feb. 3, 2006, now Pat. No. 7,856,985.

(60) Provisional application No. 60/673,914, filed on Apr. 22, 2005.

(51) Int. Cl.
*A61B 19/00* (2006.01)

(52) U.S. Cl. .............................. 128/898; 607/89; 607/9

(58) Field of Classification Search .............. 607/88–94; 606/3, 8, 9; 128/898
See application file for complete search history.

(56) References Cited

U.S. PATENT DOCUMENTS

| | | | |
|---|---|---|---|
| 5,261,904 A | 11/1993 | Baker et al. | |
| 5,395,356 A | 3/1995 | King et al. | |
| 5,810,801 A | 9/1998 | Anderson et al. | |
| 5,964,749 A | 10/1999 | Eckhouse et al. | |
| 5,976,123 A | 11/1999 | Baumgardner et al. | |
| 6,050,990 A | 4/2000 | Tankovich et al. | |
| 6,077,294 A | 6/2000 | Cho et al. | |
| 6,096,028 A | 8/2000 | Bahmanyar et al. | |
| 6,120,497 A | 9/2000 | Anderson et al. | |
| 6,159,203 A | 12/2000 | Sinofsky | |
| 6,659,999 B1 | 12/2003 | Anderson et al. | |
| 6,997,923 B2 | 2/2006 | Anderson et al. | |
| 7,856,985 B2 * | 12/2010 | Mirkov et al. ............... 128/898 |
| 2002/0151878 A1 | 10/2002 | Shimmick et al. | |
| 2002/0151879 A1 | 10/2002 | Loeb | |
| 2002/0161357 A1 | 10/2002 | Anderson et al. | |
| 2003/0040739 A1 | 2/2003 | Koop | |
| 2003/0055413 A1 | 3/2003 | Altshuler et al. | |
| 2003/0109787 A1 | 6/2003 | Black | |
| 2003/0109860 A1 | 6/2003 | Black | |
| 2003/0216719 A1 | 11/2003 | Debenedictis et al. | |
| 2004/0036975 A1 | 2/2004 | Slatkine | |
| 2004/0082940 A1 | 4/2004 | Black et al. | |
| 2004/0143247 A1 | 7/2004 | Anderson et al. | |
| 2004/0210275 A1 | 10/2004 | Town et al. | |
| 2005/0049582 A1 | 3/2005 | DeBenedictis et al. | |
| 2005/0080404 A1 | 4/2005 | Jones et al. | |
| 2005/0143719 A1 | 6/2005 | Sink | |

FOREIGN PATENT DOCUMENTS

| | | |
|---|---|---|
| JP | 11047146 A | 2/1999 |
| JP | 2001000560 A | 1/2001 |
| JP | 2003052843 A | 2/2003 |
| WO | 9737723 A1 | 10/1997 |
| WO | 9939410 A1 | 8/1999 |
| WO | 9958195 A1 | 11/1999 |
| WO | 0053113 A1 | 9/2000 |
| WO | 02/069825 A2 | 9/2002 |
| WO | 2004037068 A2 | 5/2004 |
| WO | 2005007003 A1 | 1/2005 |
| WO | 2005099369 A2 | 10/2005 |

OTHER PUBLICATIONS

Office Action dated Apr. 8, 2010 from related U.S. Appl. No. 11/347,672.
Manstein, D., et al., "Fractional Photothermolysis: A New Concept for Cutaneous Remodeling Using Microscopic Patterns of Thermal Injury," Lasers in Surgery and Medicine, 34: 426-438 (2004). cited by other.
Fractional Photothermolysis Redefines Facial Skin Regeneration Science, Aesthetic Buyers Guide, Mar./Apr. 2004, www.miinews.com, pp. 1-4.
Reliant Technologies, Inc. Physicians Guide: Understanding Faxel . TM. Laser Treatment, pp. 1-10 (2004).
Cynosure DioDerm 510(k) Notification K992765 for Cynosure, Inc. to Food and Drug Administration, dated: Aug. 16, 1999 and Aug. 20, 1999 (Additional Information).
"Selective Photothermolysis of Sebaceous Glands," Department of Health and Human Services, Public Health Service, Small Business Innovation Research Program II Grant Application, Cynosure, Inc., dated: Jul. 27, 2000, pp. 17-39 and 43-44.
PCT International Search Report—(PCT/US2006/015180) Date of Mailing: Nov. 8, 2006.

* cited by examiner

*Primary Examiner* — Ahmed Farah
(74) *Attorney, Agent, or Firm* — John M. Garvey; K&L Gates LLP

(57) ABSTRACT

Methods and apparatus for treatment, such as skin rejuvenation treatment, using non-uniform laser radiation. An output beam from a laser source is coupled into an optical system that modifies the beam to provide a large-diameter beam having a non-uniform energy profile, comprised of a plurality of high-intensity zones surrounded by lower-intensity zones within the treatment beam. A large area of tissue, preferably 7-10 mm in diameter, can be treated simultaneously, while minimizing the risk of burning or other damage to the skin.

22 Claims, 11 Drawing Sheets

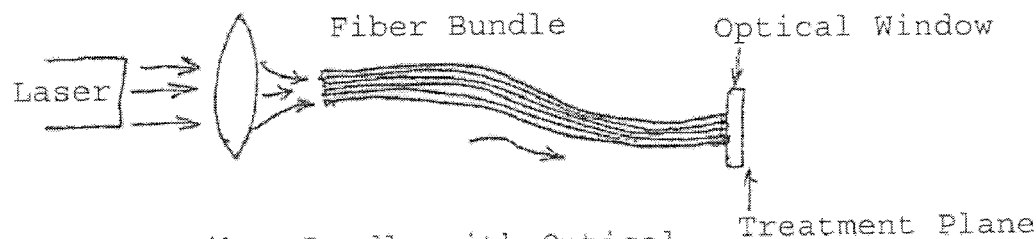
Fig.1A Long Fiber Bundle with Optical Window in contact with the skin
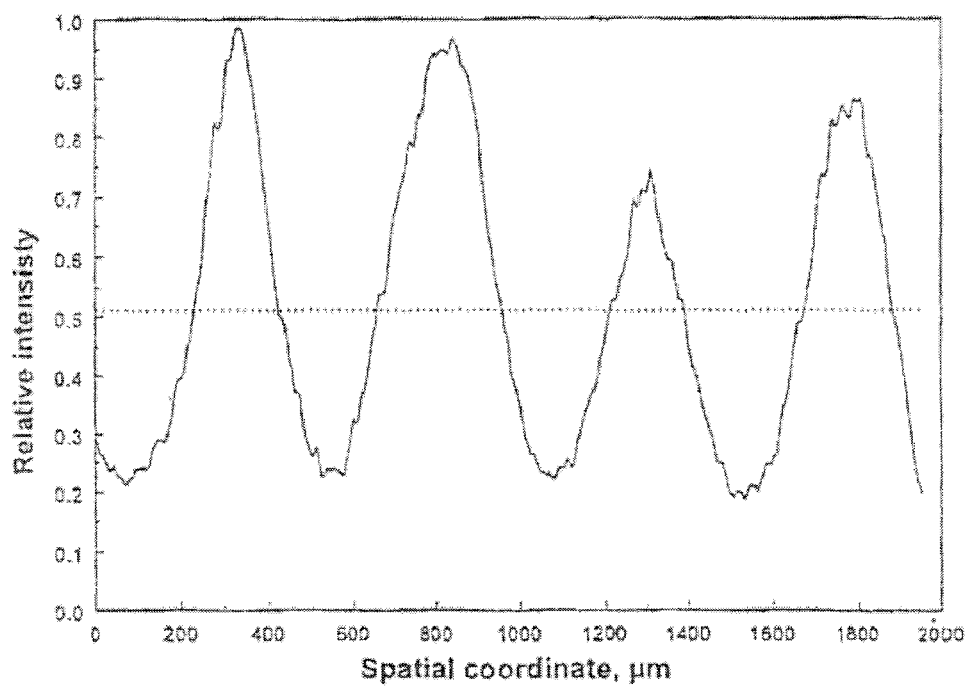
Fig. 1B

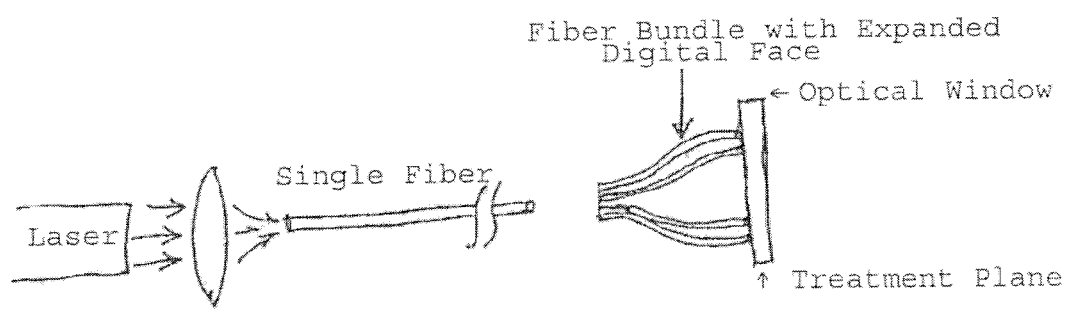
Fig. 2 Short Fiber Bundle with Expanded Face

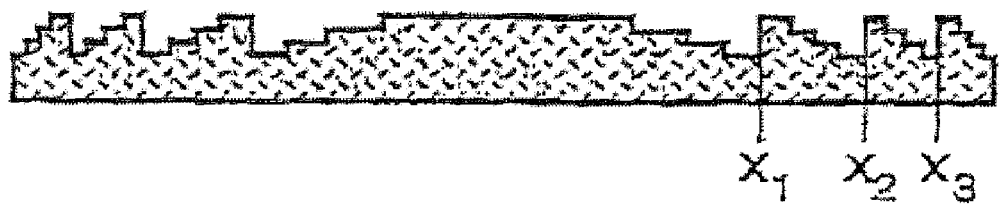
Fig. 3 Diffractive Lens with 4 levels

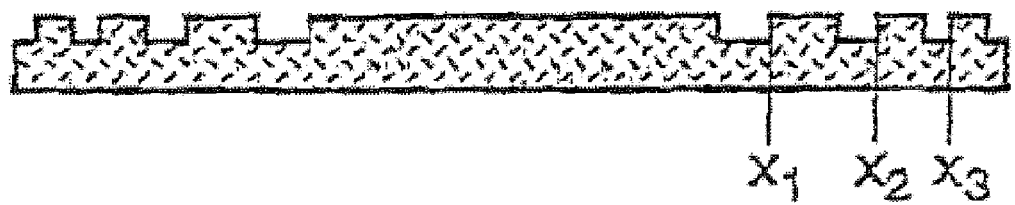
Fig. 4  Diffractive Lens with 2 levels

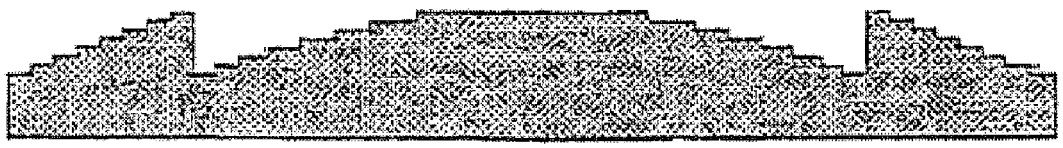
Fig. 5  Diffractive Lens with 8 levels

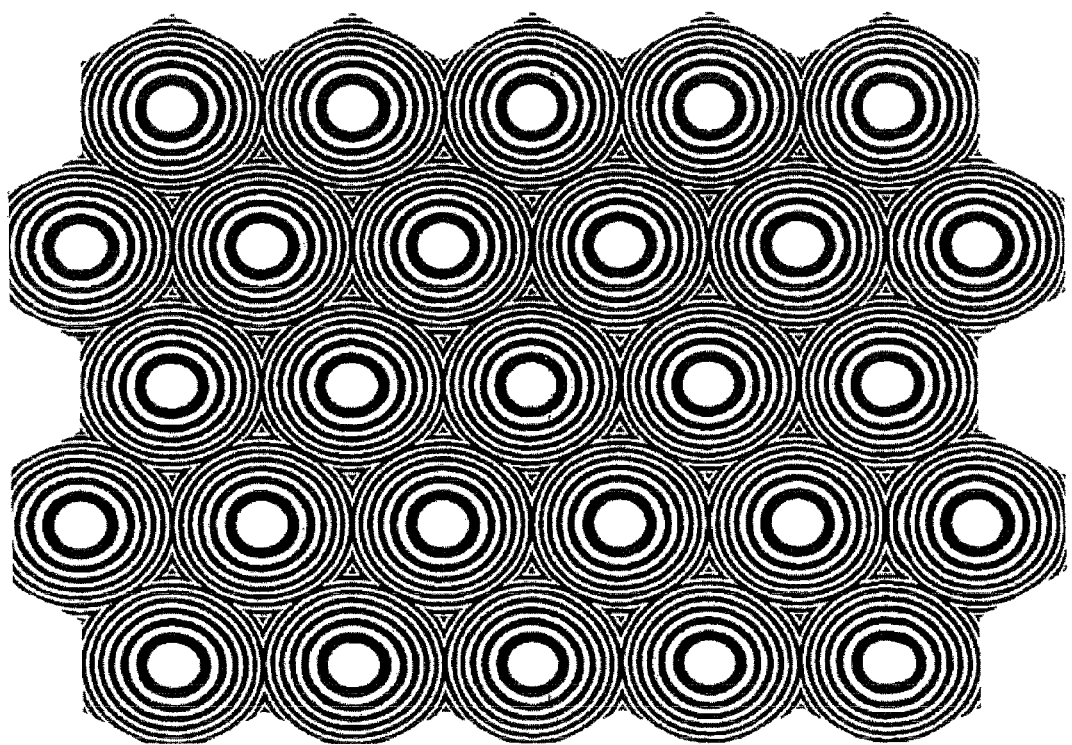
Fig. 6 Diffractive Lens Arrays arranged in hexagonal shapes

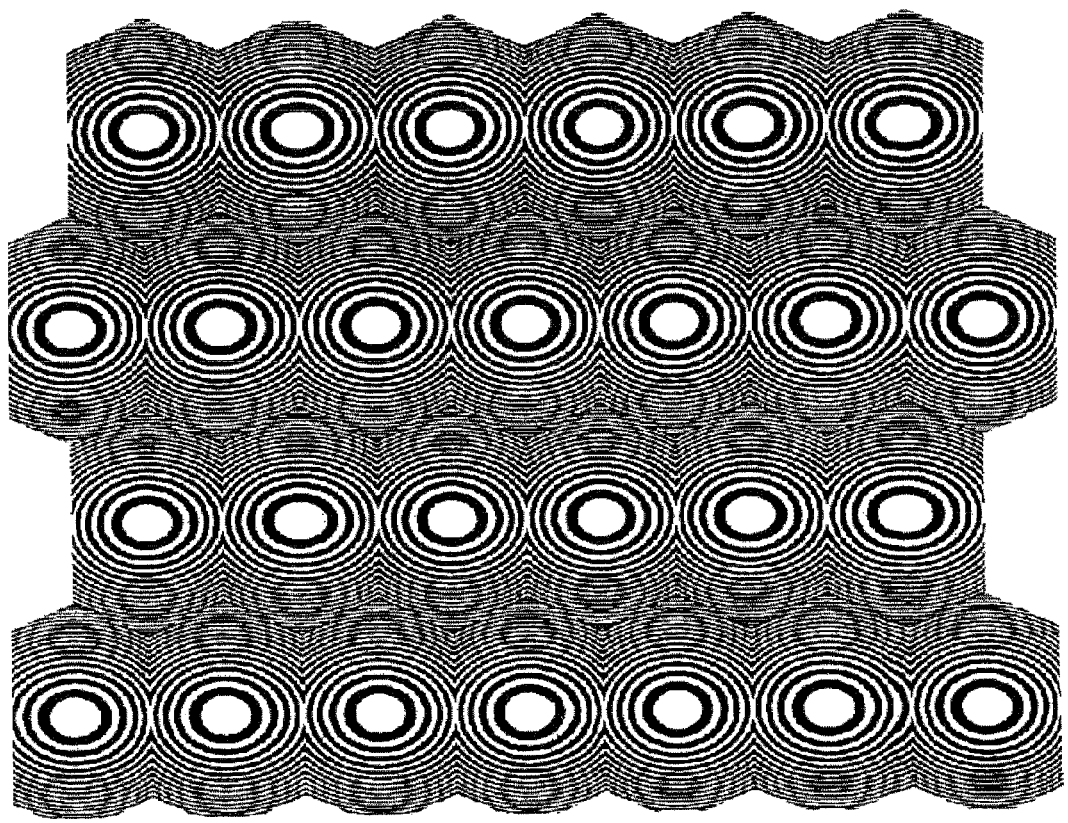
Fig. 7 Diffractive Lens Arrays arranged in elongated hexagonal shape

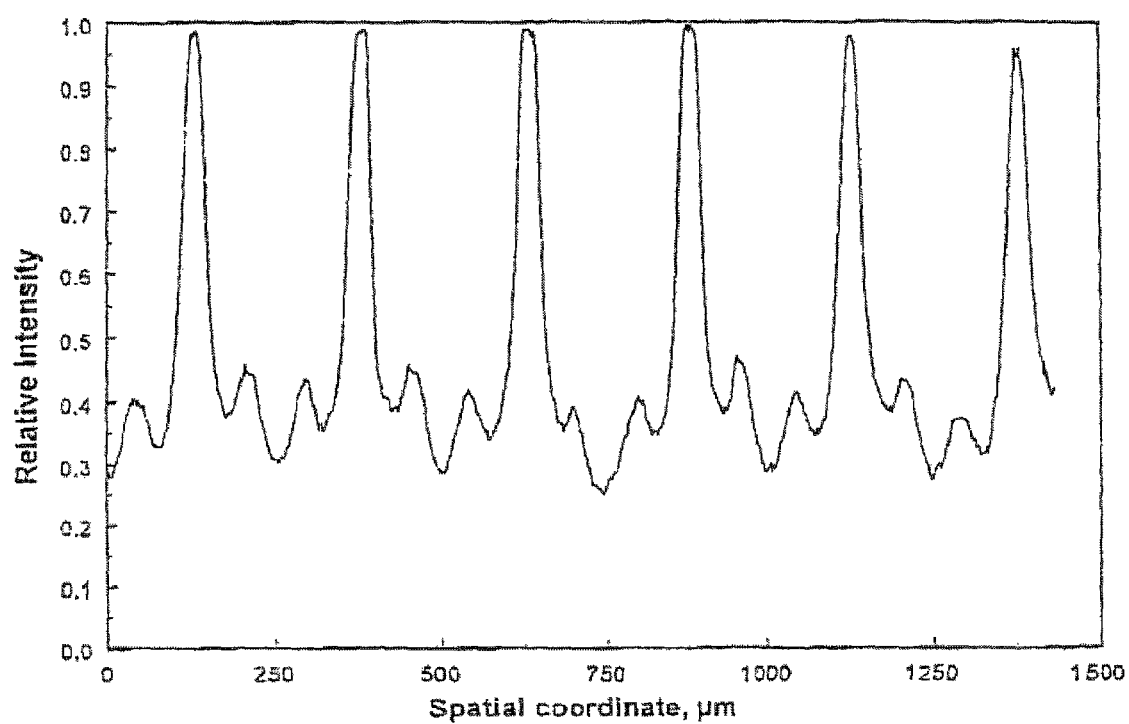
Fig. 8  Treatment Beam Profile

METHODS AND SYSTEMS FOR LASER TREATMENT USING NON-UNIFORM OUTPUT BEAM

RELATED APPLICATION

This application claims the benefit of U.S. Provisional Application No. 60/673,914, filed Apr. 22, 2005, the entire teachings of which are incorporated herein by reference.

BACKGROUND OF THE INVENTION

Plastic surgeons, dermatologists and their patients continually search for new and improved methods for treating the effects of an aging skin. One common procedure for rejuvenating the appearance of aged or photodamaged skin is laser skin resurfacing using a carbon dioxide laser. The carbon dioxide laser energy is absorbed by tissue water causing vaporization of the outer skin layer. Carbon dioxide lasers have been utilized for approximately three decades. However it has only been the past few years that these lasers have been arranged to remove only thin tissue layers with minimal heat damage to the surrounding skin. While carbon dioxide lasers may remove about 150 microns of skin, that skin may take a month or more to heal under such a procedure.

Er:YAG lasers have been utilized to ablate even thinner layers of tissue than carbon dioxide layers. However they lack the coagulation characteristics and thus allow more bleeding than a carbon dioxide laser during use.

Non-ablative skin rejuvenation is a methodology which does not take the top layer of skin off, but which uses a deep-penetrating laser to treat the layers of skin beneath the outer epidermal layer, treating unsightly vascular and pigmented lesions, and shrinking and modifying the underlying collagen, tightening the skin and reducing wrinkles to provide a more youthful appearance. This methodology however, has a low efficiency, and an aggressive cooling method must be used on to the skin so as to minimize damaging the top or upper layer thereof and also to minimize pain generation. The "fluence" or energy density used is greater than 10 joules per square centimeter and to be more effective this fluence often reaches 30 Joules per square centimeter. This level of energy often causes pain and epidermal damage.

United States Published Patent Application No. 2002/0161357 A1, by Anderson et al., discusses a method and apparatus for performing therapeutic treatment on a patient's skin by using focused radiation beams to create "islands" of treatment/damage within untreated portions of the patient's skin. However, the parameters of the treatment beam in this method are not optimal for skin rejuvenation treatment.

Yet another treatment method is disclosed in U.S. Pat. No. 6,077,294 to Cho et al., the entire teachings of which are incorporated herein by reference. This patent describes a system and methodology for noninvasive skin treatment that utilizes a pulsed dye laser having a wavelength of about 585 nanometers (nm), and an energy of less than 5 Joules per square cm. In contrast to earlier techniques which used higher-energy pulses to damage and "shrink" the collagen below the epidermis, the relatively lower energies of the beams in the '294 patent are designed to stimulate the collagen to regenerate and "fill in" valleys of the skin for a younger more clearer skin.

SUMMARY OF THE INVENTION

The present invention relates to methods and apparatus for treatment using non-uniform laser radiation. Preferably, the invention is used for skin rejuvenation treatment, in which a high-intensity portion of the laser radiation causes collagen destruction and shrinkage within select portions of the treatment area, while a lower-intensity portion of the radiation causes fibroblast stimulation leading to collagen production across other portions of the treatment area.

Preferably, the method and system of the invention utilize a solid-state laser source, such as an Nd:YAG laser. The output beam from the laser source is coupled into an optical system that modifies the beam to provide a large-diameter beam having a non-uniform energy profile, comprised of a plurality of high-intensity zones surrounded by lower-intensity zones within the treatment beam. The higher-intensity zones heat select portions of the target tissue to temperatures sufficient for a first treatment (e.g. collagen shrinkage), while the lower-intensity zones provide sufficient energy to the surrounding tissue for a second treatment (e.g. stimulated collagen production). Thus, a large area of tissue, preferably 7-10 mm in diameter, can be treated simultaneously, while minimizing the risk of burning or other damage to the skin.

In one embodiment, the invention uses a fiber bundle to provide a non-uniform energy output beam. In another embodiment, the invention uses a diffractive lens array to produce the non-uniform output beam.

A method of treating human skin in accordance with one aspect of the invention comprises generating an output beam from a laser source, such as an Nd:YAG laser; coupling the beam into an optical system that modifies the beam to provide a treatment beam having a non-uniform energy profile, the treatment beam comprised of a plurality of high-intensity zones surrounded by low-intensity zones within the treatment beam; and directing the treatment beam to a target tissue area such that the high-intensity zones heat select portions of the target tissue to temperatures sufficient for a first treatment, while the lower-intensity zones provide sufficient energy to the surrounding tissue for a second treatment. Preferably, the first treatment comprises collagen shrinkage and the second treatment comprises collagen stimulation. The output beam can have a wavelength between about 1.3 to 1.6 microns, and preferably between about 1.41 and 1.44 microns, and a pulse duration between 0.1 and 100 milliseconds, and preferably between about 1 and 5 milliseconds. The average fluence of the treatment beam can be less than about 10 $J/cm^2$. Generally, the average fluence of the treatment beam is between about 5-6 $J/cm^2$. The average fluence in the lower-intensity zones is generally on the order of 2-3 $j/cm^2$.

The optical system can comprise a fiber bundle, having 1000 to 2000 separate fibers, for instance, and a focusing lens for coupling the beam into the fiber bundle. An optical window, preferably between 1 and 5 mm thick, can be located at the distal end of the bundle, the optical window permitting the beams emitted from each fiber in the bundle to diverge and partially overlap with one another before they reach the target tissue. In certain embodiments, a transport fiber can carry the output beam from the laser source to the fiber bundle, and the fiber bundle can be located in a handpiece.

In another embodiment, the optical system can comprise a diffractive lens array, preferably comprised of about 2000 or less lenses, arranged in an optical path between a laser source and the treatment area, such that each lens in the array provides a high-intensity zone surrounded by a low intensity zone of radiation. Each lens in the array can have a diameter of between about 150 and 450 microns, and the entire lens array can have a diameter of between about 7 and 10 mm. Preferably, the average fluence of the laser output beam is less than about 10 $J/cm^2$.

In another embodiment, a laser system of the invention comprises a laser source that generates an output beam; and an optical system that modifies the output beam to provide a treatment beam having a non-uniform energy profile, the treatment beam being comprised of a plurality of high-intensity zones surrounded by low-intensity zones within the treatment beam, such that the high-intensity zones heat select portions of a target tissue to temperatures sufficient for a first treatment, while the lower-intensity zones provide sufficient energy to the surrounding tissue for a second treatment. The laser source can be an Nd:YAG laser, and generally produces an output beam having a wavelength between about 1.3 to 1.6 microns, and preferably between about 1.41 and 1.44 microns, and a pulse duration between 0.1 and 100 milliseconds, preferably between about 1 and 5 milliseconds. The optical system can comprise a fiber bundle, preferably with an optical window between the distal end of the bundle and the target tissue. Alternatively, the optical system can include a diffractive lens array in the optical path between the source and the treatment area, such that each lens in the array provides a high-intensity zone surrounded by a low intensity zone of radiation.

According to another embodiment, a laser system comprises a laser source that generates an output beam; a fiber bundle comprising a plurality of individual fibers, the fiber bundle having a proximal end and a distal end; a focusing lens for coupling the output beam into a proximal end of the fiber bundle; and an optical window at the distal end of the fiber bundle, the optical window permitting the beams emitted from each fiber in the bundle to diverge as the beam passes through the optical window so that each beam partially overlaps with the beam(s) from adjacent fibers in the bundle. The optical window can comprise a transparent material, such as glass, or could comprise a spacer having an empty space between the distal end of the fiber bundle and the treatment area.

According to yet another embodiment, a laser system comprises a laser source that generates an output beam; and a diffractive lens array arranged in an optical path between a laser source and a treatment area, such that each lens in the array provides a high-intensity zone surrounded by a low intensity zone of radiation.

The present invention provides a laser treatment which covers a large area of the patient, is characterized by high-absorption of the laser radiation and lower peak energies, which results in minimal risk of skin damage. In one aspect, the present invention advantageously accomplishes stimulated collagen production as well as collagen shrinkage simultaneously in a single treatment area. In addition to skin rejuvenation treatment, the principles of the invention can also be extended for use in other types of optical radiation treatments, including, without limitation, treatment of acne, hair removal, and treatment of vascular or pigmented lesions.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A illustrates a laser treatment system comprising a fiber bundle and optical window;

FIG. 1B is a plot of the beam profile on the skin for the laser treatment system of FIG. 1A;

FIG. 2 illustrates a laser treatment system comprising a short fiber bundle with expanded distal face;

FIG. 3 shows a diffractive lens having four levels;

FIG. 4 shows a diffractive lens having two levels;

FIG. 5 shows a diffractive lens with eight levels;

FIG. 6 shows a diffractive lens array having a hexagonal pattern;

FIG. 7 shows a diffractive lens array having an elongated hexagonal pattern;

FIG. 8 shows a treatment beam profile for a diffractive lens array;

DETAILED DESCRIPTION OF THE INVENTION

Figure 9:
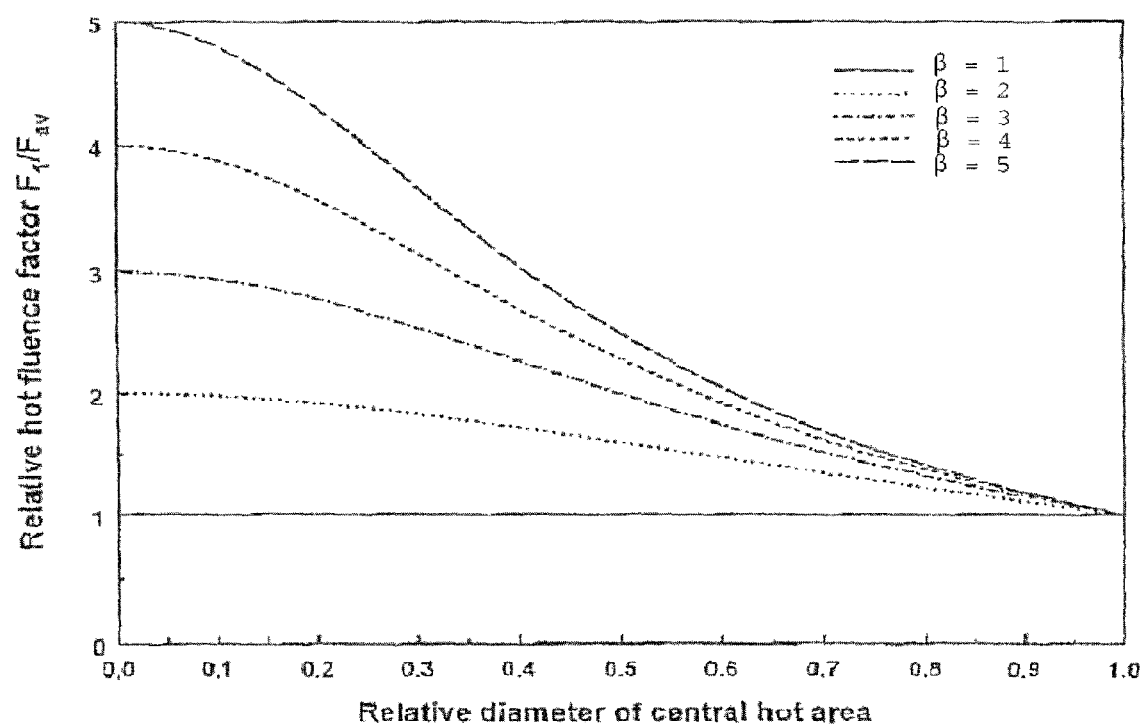
FIG. 9 shows a plot of the relative hot area fluence factor, $F_1/F_{av}$, as a function of the relative diameter of the central hot area, d/D for a diffractive lens array in accordance with one aspect of the invention.

A description of preferred embodiments of the invention follows.

As shown in FIG. 1A, the apparatus includes a laser source that emits an output beam. The beam is coupled into a bundle of optical fibers using one or more focusing lenses. The bundle preferably contains between 1000 and 2000 separate fibers. Typically, each fiber has a diameter of about 100-200 microns. The output laser beam is thus directed to 1000-2000 smaller beams, each of which traverses the length of the fiber bundle in individual optical fibers. The fiber bundle terminates at its distal end at an optical window that can be held in direct contact with the patient's skin. The window is approximately 1-5 mm thick, and protects the output face of the fiber bundle from contamination, and also permits the beam emitted from each fiber to diverge before it reaches the patient's skin, preferably so that each beam partially overlaps with the beam(s) from adjacent fibers in the bundle.

The fibers in the bundle can be packed together tightly, or can be spaced apart from each other using mechanical spacers. The use of mechanical spacers at the distal end of the bundle spreads the energy from the bundle over a larger area, and helps to reduce the pain sensation for the patient. In general, the combined spot size on the skin from all the fibers in the fiber bundle is between approximately 7 and 10 mm in diameter.

In a preferred treatment method for the embodiment of FIG. 1A, the laser source, which is preferably an Nd:YAG laser, produces an output laser pulse having a wavelength of between 1.3 and 1.6, preferably between about 1.40 and 1.44 microns, and a pulse duration of between 0.1 and 100 milliseconds, preferably between about 1 and 5 milliseconds. Because the laser operates at wavelengths that are well-absorbed by the skin, the laser can operate at relatively low energies, and minimize the risk of burning or damage to the skin.

In operation, the optical window is held against the skin of the patient, and the laser source is energized to produce a pulse of laser light that travels from the source through the fiber bundle and the optical window, and penetrates into the patient's skin. Since the optical window is approximately 1-5 mm thick, the window also serves as a spacer between the output end of the fiber bundle and the skin of the patient. Thus, as the laser light is emitted from each fiber in the bundle, the light is permitted to diverge as it travels through the window to the patient's skin. In a preferred embodiment, the fibers are approximately 100-200 microns in diameter, and the beam emitted from each fiber, after passing through the window, produces a spot between 150-900 microns in diameter on the patient's skin. Because of the diverging nature of light emitted from an optical fiber, the light at the center of each spot will be relatively high-energy light, while the light at the periphery of each spot will have significantly lower energy. Thus, over a combined spot size of 7 to 10 mm for the entire fiber bundle, there are approximately 1000 to 2000 smaller treatment spots, generally about 150-900 microns in diameter, each consisting of a higher-fluence "hot spot" at the center of the spot surrounded by a lower-fluence "cooler zone" of radiation. The energy at the central "hot spot" is sufficient to shrink the underlying tissue, damage the collagen and produce collagen shrinkage. In general, the energy at the high-intensity zones, or "hot spots" is sufficient to raise the temperature of the target tissue to 70° C. or higher. However, the radiation in "cooler zone" surrounding the hot spot is generally not sufficient to damage the tissue and cause collagen shrinkage in the tissue underlying these areas. In these lower-intensity "cooler zones," the energy provided will only raise the temperature of the skin by a few degrees (or perhaps result in no appreciable temperature rise), and thus will not damage or even "shock" the tissue. However, this lower-intensity radiation is generally more appropriate or preferred to stimulate the fibroblasts in the tissue to produce collagen and "fill in" the skin for a younger more clearer skin In a preferred embodiment, the fibers in the bundle are arranged so that the spot sizes of radiation from each fiber abut or partially overlap with the spots from the adjacent fibers in the bundle on the patient's skin. In this way, the invention can simultaneously provide two modes of skin rejuvenation treatment: higher-energy collagen shrinkage treatment in the "hot spots" at the center of each output spot from the fiber bundle, and overall stimulated collagen production throughout the entire area of the combined fiber-bundle output beam.

An example of a laser treatment method using a fiber bundle delivery system is illustrated in FIG. 1B, which is a plot of the relative intensity on the skin as a function of location on the skin for four fibers in the bundle. In practice, the fiber bundle will consist of 1000-2000 individual fibers, in a regularly-spaced arrangement to form a bundle. In this embodiment, the center-to-center distance between adjacent fibers in the bundle is approximately 500 microns. The diameter of each fiber is approximately 200 microns, and the numerical aperture (NA) of the fibers is approximately 0.2. The total diameter of the fiber bundle is approximately 9 millimeters. The laser energy emitted from each fiber diverges as it passes through the transparent window, so that the spot size on the skin from each fiber is at least about 250 microns in diameter. Thus, the spots from each fiber generally abut or partially overlap with the spots from the adjacent fibers in the bundle. This is shown in FIG. 1B, where it can be seen that the whole area is treated with at least a low-intensity pulse, while the areas at the center of each spot receive a significantly higher dose of energy. The dotted line represents the average intensity throughout the treatment area. In this example, the peak fluence on the skin at the center of each spot is approximately 9 J/cm$^2$, while the fluence at the periphery of each spot is approximately 2 J/cm$^2$. The total area fluence is approximately 5 J/cm$^2$.

The fluence(s) received at various portions of the treatment area can be varied and controlled by, for instance, raising or lowering the total energy output from the laser source, changing the center-to-center distances between fibers in the bundle, using different diameter fibers, using fibers with a different NA to change the divergence of the beam and/or altering the thickness of the optical window to allow for a greater or lesser amount of beam divergence. The beam profile can thus be optimized for a variety of different conditions and laser treatment methods.

FIG. 2 shows yet another embodiment that is similar to the embodiment of FIG. 1, except that instead of a long-fiber bundle coupling the laser output beam from the source to the optical window, this embodiment uses a single transport fiber to carry the laser energy from the laser source to a handpiece containing a shorter fiber bundle. At the handpiece, the output laser pulse from the single fiber is coupled into the short fiber bundle. As in the prior embodiment, the short fiber bundle is comprised of a plurality of separate optical fibers, preferably 1000 to 2000 fibers. The short fiber bundle has a smaller bundle diameter at its proximal end to allow the output light from the single transport fiber to efficiently couple into the bundle. The fiber bundle "fans out" from its proximal end to its distal end, using, for example, mechanical spacers, to provide an expanded face at it's output. Preferably, the expanded face has a diameter of between approximately 7 to 10 mm, and is coupled to an optical window, as in the embodiment of FIG. 1. The embodiment of FIG. 2 preferably uses the same treatment parameters as those described in connection with FIG. 1.

Turning now to FIGS. 3-8, yet another embodiment of the invention is illustrated which uses a diffractive lens array to provide non-uniform heating in the target tissue. A multilevel diffractive lens consists of a number of concentric rings made of optically transparent material with variable thicknesses. The top surface of each concentric ring is flat so the refractive effects are negligible. The variable-thickness rings give rise to a spatial phase delay pattern on a propagating incident optical beam. The propagating optical beam carries the spatial phase delay pattern past the plane of the diffractive lens and produces an illumination pattern of spatially variable optical intensity. The optical intensity is high at geometrical points that meet the conditions for constructive interference and low at the points that meet the conditions for destructive interference. In general the design of a diffractive lens is optimized so that the principal diffraction maximum (or minimum) would be on the optical axis at a distance f from the plane of the lens. The distance f is the focal length of the lens. In general the goal of the diffractive lens design is to increase the fraction of the incident power in the principal diffraction maximum. However, that fraction is always less than 1 depending on the number of levels, the F-number of the lens and other design parameters. In fact, it is possible to design the diffractive lens pattern so that any fraction (less than 1) of the incident power would be in the principal maximum and the rest of the power would be distributed in the secondary maxima.

Various examples of multi-level diffractive lenses are shown in cross-sectional views in FIGS. 3-5. FIG. 3 shows a diffractive lens having four levels; FIG. 4 shows a diffractive lens having two levels; and FIG. 5 shows a diffractive lense with eight levels.

In one embodiment of the present invention, a laser treatment apparatus and method utilizes plurality of diffractive lenses that are arranged in an array to produce an output beam having a non-uniform energy profile. More specifically, the diffractive lens array is arranged in an optical path between a laser source and the treatment area, such that each lens in the array provides for an area of higher-fluence "hot spots" surrounded by lower-fluence regions of radiation. In a skin rejuvenation treatment, for example, the higher-energy areas provide sufficient heating to damage and shrink collagen in the "hot spots," while the lower-intensity radiation regions outside of these hot spots overlap and combine to stimulate collagen regrowth over the entire treatment area.

In this embodiment, the laser source preferably produces a pulse of radiation having a wavelength between approximately 1.3 and 1.6 microns, preferably between 1.40 and 1.44 microns, and a pulse duration of between about 0.1 and 100 milliseconds, preferably between 1 and 5 milliseconds. The laser source can be an Nd:YAG laser, for example. An optical system carries the beam from the laser source to the treatment area. The diffractive lens array is preferably arranged at the distal end of the optical system, adjacent to the patient's skin. The array comprises a plurality of separate diffractive lenses adjacent to one another. In general, there are 2000 or less lenses in an array, and preferably about 1800 lenses. Each lens is between about 150 and 450 microns in diameter, and is preferably about 250 microns in diameter. The entire array of diffractive lenses is generally about 7 to 10 mm in diameter. The array directs the input beam from the laser source (which is preferably also about 7-10 mm in diameter) into a plurality of higher-intensity "hot spots," corresponding to the central portion of each individual lens in the array, and lower intensity regions surrounding each hot spot. The combined effect in the patient's tissue is to produce a plurality of higher-intensity zones in the skin corresponding to the center of each diffractive lens surrounded by areas of lower-intensity radiation. This is shown in the treatment beam profile of FIG. 8. As can be seen in this graph, the entire treatment area receives at least a low level of treatment radiation, with certain spaced-apart portions receiving a higher dose of laser radiation. In the case of skin rejuvenation, for example, the laser energy penetrates deep into the collagen layer, where the collagen is heated to shrinkage temperatures in the "hot spots," while the entire treatment area is treated to effect collagen regeneration. In addition to skin rejuvenation treatment, the diffractive lens array can be optimized for use in other applications, such as treatment of acne and hair removal. A different beam profile from the diffractive lens array can be used for different applications.

The diffractive lens is considered to be irradiated by an average uniform fluence, $F_{av}$, determined by the laser fluence setting selected by the user. In general, the average fluence of the laser in this embodiment is less than about 10 J/cm², and is preferably about 9 J/cm². For purposes of illustration, each diffractive lens with diameter D is assumed to have a simplified design so that it produces a hot area with diameter, d, assumed to have uniform fluence, $F_1$, and a periphery having a uniform fluence, $F_2$. The lens design is assumed to produce a fluence ratio, β, of the hot area versus the periphery, $\beta = F_1/F_2$. Under these simplifying assumptions, is it possible to derive a simple formula to approximate the hot area fluence, $F_1$:

$$\frac{F_1}{F_{av}} = \frac{1}{\left(\frac{d}{D}\right)^2 + \frac{1}{\beta}\left[1 - \left(\frac{d}{D}\right)^2\right]} \quad \text{(Eq. 1)}$$

FIG. 9 shows a plot of the relative hot area fluence factor, $F_1/F_{av}$, as a function of the relative diameter of the central hot area, d/D. As an example, if the diffractive lens is designed to have β=5, with diameter D=250 µm, hot area diameter d=100 µm, and the laser is selected to have average fluence $F_{av}$=9 J/cm², then the hot area fluence is $F_1$=3.05×9 J/cm²=27.4 J/cm².

FIGS. 6 and 7 illustrate two exemplary embodiments of a diffractive lens array according to the invention. In FIG. 6, the diffractive lenses are arranged in a hexagonal pattern. In FIG. 7, the lenses are arranged in an elongated hexagonal pattern.

Figure 10:
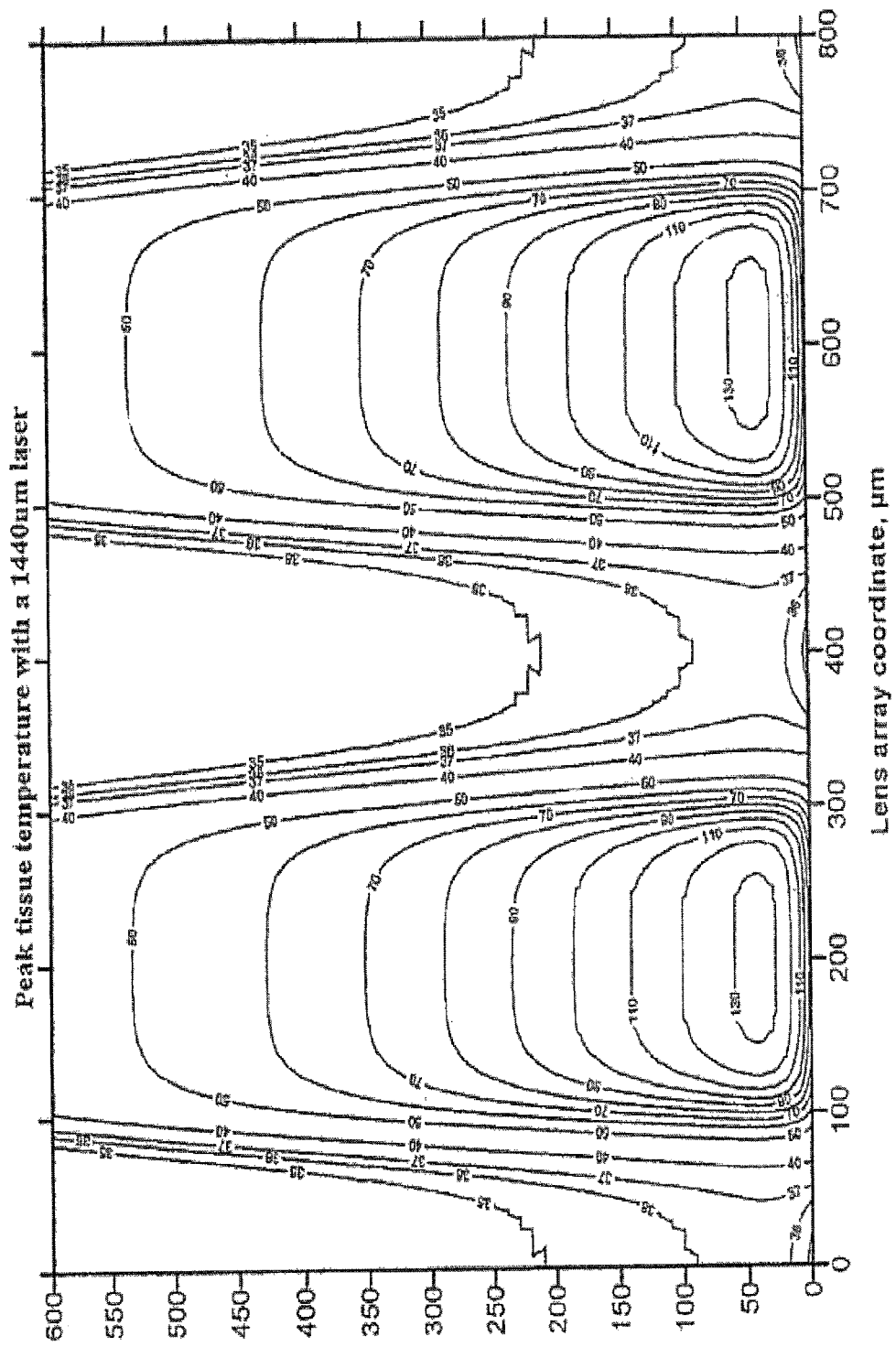
FIG. 10 shows the temperature profile of skin treated with a non-uniform output beam from a diffractive lens array.

FIG. 10 shows the peak tissue temperature distribution for a portion of skin irradiated with a 1440 nm laser through a diffractive lens array. As can be seen from the graph, a first diffractive lens is centered at about 200 µm, and a second diffractive lens is centered at about 600 µm on the horizontal axis. As can be seen from this graph, there is an area of tissue about 200 µm wide centered on each of the diffractive lenses that is heated to relatively high peak temperatures (e.g., 70° C. or higher). This high-temperature zone extends from essentially the surface of the skin to a depth of about 350 µm. As discussed above in connection with the fiber-bundle embodiment of FIGS. 1A and 1B, these temperatures are sufficient to cause collagen shrinkage. Outside of these high-temperature treatment zones, the peak temperatures quickly drop off. For example, in the area between about 300 µm and 500 µm on the horizontal axis, the peak skin temperatures are generally between 35° C. (or less) and 50° C., and are generally less than about 40° C. As previously discussed, these lower intensity zones provide collagen stimulation treatment.

Figure 11:
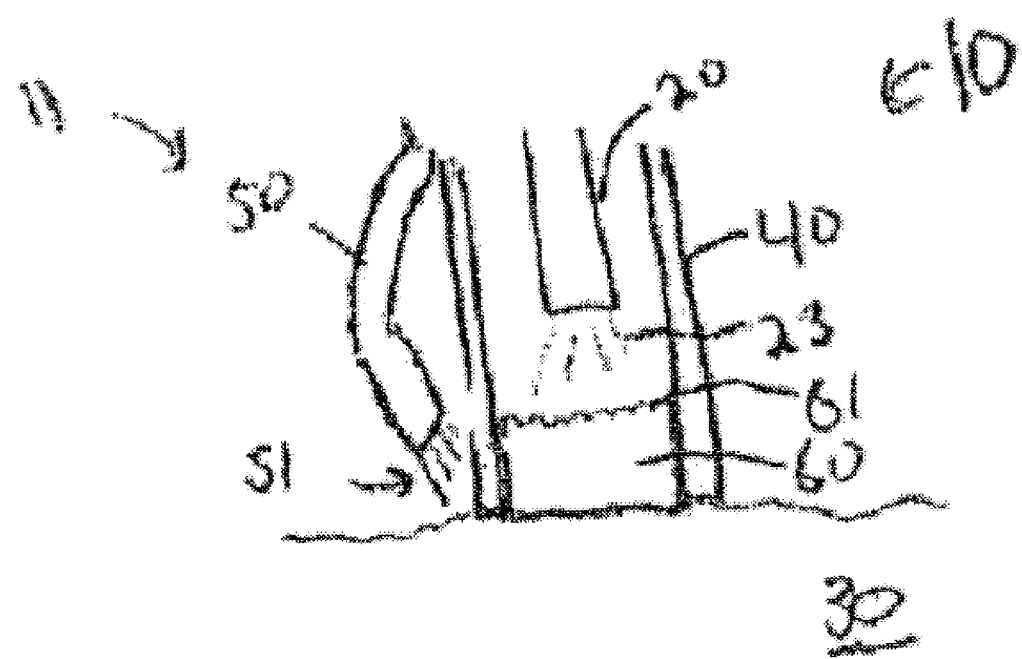
FIG. 11 shows a tip of a laser treatment handpiece having a cooling mechanism.

FIG. 11 is a cross-sectional view of a tip 10 of a laser treatment apparatus having a diffractive lens array for providing an output beam having a non-uniform energy profile. The operator applies the tip 10 directly against the patient's skin 30. A laser source (not shown) is energized to produce an output beam 23, and the output beam is carried to the tip 10 by an optical fiber 20. The output beam 23 is emitted from the end of optical fiber 20, and is directed to diffractive lens array 61. Adjacent to the diffractive lens array 61 is an optical window 60 that directly contacts the patient's skin 30. The optical window 60 is similar to the optical window described in connection with FIG. 1, and functions as a spacer between the output end of the fiber bundle and the skin of the patient. The optical window 60 can be integral with the diffractive lens array 61. Preferably, the window is made of a good thermal conductive material, such as glass. The optical fiber 20, lens array 61, and optical window 60 are all enclosed in a tip housing 40, which is preferably a cylindrically-shaped housing. The tip housing 40 can be made of plastic. Outside the tip housing 40 is a cooling mechanism 11. Preferably, the cooling mechanism 11 comprises a conduit 50 that carries cooled air 51 from a cooled air source (not shown) to the tip 10 of the treatment apparatus. The conduit 50 preferably includes an outlet that is angled with respect to the tip housing 40, so that cooled air 51 is directed at the distal end of the tip housing 40 (i.e. where the tip 10 interfaces with the patient's skin 30). This arrangement provides effective cooling of the skin during laser treatment. Although the tip 10 and cooling mechanism 11 are shown here in connection with the diffractive lens array embodiment of FIGS. 3-8, it will be understood that this design may also be employed with a laser apparatus having a fiber bundle, such as shown and described in connection with FIGS. 1 and 2.

While this invention has been particularly shown and described with references to preferred embodiments thereof, it will be understood by those skilled in the art that various changes in form and details may be made therein without departing from the scope of the invention-encompassed by the appended claims.

What is claimed is:

1. A method for treating human tissue, comprising:
generating an output beam from a laser source;
coupling the beam into an optical system that modifies the beam to provide a treatment beam having a non-uniform energy profile, said non-uniform energy profile being comprised of regions of relatively high energy per unit area within a substantially uniform background region of relatively low energy per unit area in comparison to the regions of relatively high energy per unit area; and directing the treatment beam to a target tissue such that the regions of relatively high energy per unit area of the beam illuminate portions of the target tissue and deliver sufficient energy to such portions of the target tissue to heat such portions of the target tissue to a first temperature $T1$, and wherein the substantially uniform background region of relatively low energy per unit area of the beam illuminates the remaining portion of the target tissue and delivers sufficient energy to such remaining portion of the target tissue to heat the remaining portion of the target tissue to a second temperature $T2$, wherein $T2$ is less than $T1$.

2. The method of claim 1, wherein the treatment beam regions of relatively high energy per unit area heat select portions of the target tissue to a first temperature $T1$ of 35 degrees C. or higher.

3. The method of claim 1, wherein the laser source comprises an Nd:YAG laser or a diode laser.

4. The method of claim 1, wherein the wavelength of the output beam is between about 1.3 microns and 1.6 microns.

5. The method of claim 4, wherein the wavelength of the output beam is between about 1.40 and 1.44 microns.

6. The method of claim 1, wherein the treatment beam at the target tissue area has a diameter between about 5 and 10 mm.

7. The method of claim 6, wherein the average fluence of the treatment beam at the target tissue area is less than about 10 J/cm2.

8. The method of claim 1, wherein the output beam has a pulse duration of between 0.1 and 100 milliseconds.

9. The method of claim 8, wherein the output beam has a pulse duration of between 20 and 80 milliseconds.

10. The method of claim 1, wherein the optical system comprises a fiber bundle.

11. The method of claim 10, wherein the fiber bundle comprises 1000 to 2000 fibers.

12. The method of claim 10, wherein the optical system comprises a focusing lens for coupling the output beam into a proximal end of the fiber bundle, and an optical window between the distal end of the fiber bundle and the target tissue, the optical window permitting the beam emitted from each fiber in the bundle to diverge before it reaches the target skin so that each beam partially overlaps with the beam(s) from adjacent fibers in the bundle.

13. The method of claim 12, wherein the optical window is between 1 and 5 mm thick.

14. The method of claim 10, wherein the average fluence of the treatment beam is less than about 10 J/cm2.

15. The method of claim 10, wherein the optical system comprises a transport fiber that carries the output pulse from the laser source to a handpiece containing the fiber bundle.

16. The method of claim 1, wherein the optical system comprises a diffractive lens array such that each lens in the array provides a region of relatively high energy per unit area, the regions of relatively high energy per unit area within a substantially uniform background region of relatively low energy per unit area in comparison to the regions of relatively high energy per unit area.

17. The method of claim 16, wherein the diffractive lens array comprises about 2000 or less lenses in the array.

18. The method of claim 17, wherein each lens is between about 150 and 1000 microns in diameter.

19. The method of claim 16, wherein the diffractive lens array is between 5 and 10 millimeters in diameter.

20. The method of claim 16, wherein the average fluence of the laser output beam is less than about 10 J/cm2.

21. The method of claim 16, wherein the output beam has a pulse duration between 0.1 and 100 milliseconds.

22. The method of claim 21, wherein the output beam has a pulse duration between 20 and 80 milliseconds.

* * * * *